United States Patent
Kobayashi et al.

[11] Patent Number: 5,482,609
[45] Date of Patent: Jan. 9, 1996

[54] SOLID ELECTROLYTE GAS SENSOR

[75] Inventors: Tsuyoshi Kobayashi; Misa Saitoh, both of Nagano, Japan

[73] Assignee: Shinko Electric Industries Co., Ltd., Nagano, Japan

[21] Appl. No.: 236,021

[22] Filed: Apr. 26, 1994

[30] Foreign Application Priority Data

Apr. 27, 1993 [JP] Japan ................................ 5-100721
May 28, 1993 [JP] Japan ................................ 5-126944
May 28, 1993 [JP] Japan ................................ 5-126945

[51] Int. Cl.$^6$ ............................................. G01N 27/407
[52] U.S. Cl. ............... 204/412; 204/153.14; 204/153.18; 204/153.19; 204/421; 204/424; 204/426; 205/324; 264/56; 427/431
[58] Field of Search ........................... 204/153.18, 412, 204/421–429, 153.14, 153.19

[56] References Cited

U.S. PATENT DOCUMENTS

| | | | |
|---|---|---|---|
| 4,107,019 | 8/1978 | Takao et al. | 204/426 |
| 4,388,155 | 6/1983 | Chamberland et al. | 204/427 |
| 4,568,445 | 2/1986 | Cates et al. | 204/416 |
| 4,571,285 | 2/1986 | Nakazawa et al. | 204/425 |
| 4,715,944 | 12/1987 | Yangida et al. | 204/426 |
| 4,976,991 | 12/1990 | Ammende et al. | 204/429 |
| 5,186,810 | 2/1993 | Nagai et al. | 204/426 |

OTHER PUBLICATIONS

S. Yao et al., "Solid Electrolyte Carbon Dioxide Sensor Using Sodium–Ion Conductor and $Li_2CO_3$–$BaCO_3$ Electrode", Jpn. J. Appl. Phys. vol. 31, pp. L197–L199.(Feb. 15, 1992).

Y. Yan et al., "Solid State Sensor for Sulfur Oxides Based on Stabilized Zirconia and Metal Sulphate", Chemistry Letter, pp. 635–638, (1992) month unavailable.

*Primary Examiner*—T. Tung
*Attorney, Agent, or Firm*—Michael N. Meller

[57] ABSTRACT

A solid electrolyte gas sensor comprising: a base plate of a solid electrolyte, on which are disposed a detecting electrode for detecting a selected gas, a reference electrode, and a conductor portion for external connection such as an outer lead.

A process of producing a joined body of a ceramic member and a hard-to-sinter oxyacid salt crystal, the process comprising the steps of: impregnating a melt of a hard-to-sinter oxyacid salt such as a sulphate or a carbonate into a porous ceramic plate having micropores extending through the entire thickness thereof; then cooling the impregnated ceramic plate to form a composite plate composed of the ceramic plate with the micropores filled with a crystal of the hard-to-sinter oxyacid salt; and joining the composite plate to a ceramic base.

A process of producing a hard-to-sinter oxyacid salt crystal on, and joined to, a ceramic base, the process comprising the steps of: forming a metal film on a ceramic base; anodizing the metal film to form a porous oxide film having numerous micropores extending through the entire thickness thereof; melting a hard-to-sinter oxyacid salt such as a sulphate or a carbonate on the porous oxide film, thereby causing the porous oxide film to be impregnated with a melt of the salt; and then cooling the ceramic base, together with the oxide film, to form a crystal of the hard-to-sinter oxyacid salt joined to the ceramic base.

5 Claims, 5 Drawing Sheets

SOLID ELECTROLYTE GAS SENSOR

BACKGROUND OF THE INVENTION

1. Field of the Invention

The present invention relates to a solid electrolyte gas sensor using a solid electrolyte material such as zirconia ceramic.

The present invention also relates to a process of producing a joined body of a ceramic member and a crystal of a hard-to-sinter oxyacid salt such as a sulphate or a carbonate.

The present invention also relates to a process of producing a hard-to-sinter oxyacid salt such as a sulphate and a carbonate joined to a ceramic member.

2. Description of the Related Art

Because of their high ion conductivity, solid electrolyte materials are advantageously used in gas sensors. For example, zirconia ceramic, which has a oxygen ion conductivity sufficient for an oxygen gas sensor, is actually used as a sensor for detecting an oxygen concentration.

FIG. 1 shows an oxygen gas sensor comprising zirconia ceramic, in which a tube 104 of zirconia ceramic has electrodes 105 and 106 on the inner and outer side walls thereof, respectively, to detect an electromotive force between the electrodes 105 and 106 while a selected gas is allowed to flow through the tube 104.

This oxygen gas sensor detects an oxygen gas concentration by measuring an electromotive force generated between both sides of the wall of the zirconia ceramic tube 104 because of migration of oxygen ions through the zirconia ceramic wall when oxygen concentrations are different on both sides of the wall. Therefore, to improve the detecting efficiency of the gas sensor, the ion conductivity must be improved, so that a gas sensor using a solid electrolyte is actually operated while being heated at several hundreds of degrees centigrade.

Thus, a gas sensor using a solid electrolyte material need be heated to an elevated temperature when operated, so that the shown oxygen gas sensor has a nichrome wire heater 107 surrounding and heating the zirconia ceramic tube 104. The numeral "108" denotes a thermocouple. This causes a first problem that a gas sensor is large and is complicated in structure.

Sulphates, carbonates, nitrates, etc., have a poor sinterability and are difficult to form into a sintered body or, if sintered, have a poor durability, although they are used to make various devices including solid state gas sensors.

Moreover, crystals of these salts, when produced by heating to a liquid and subsequent cooling to a solid, involve cracks induced by a change in the crystal structure occurring upon a phase transformation at a specific temperature. Such cracks are detrimental to those devices that need a hermetic seal.

Sulphates, carbonates, nitrates, etc., are easily decompose to form SOx, COx, NOx, etc. at elevated temperatures and decompose by reaction with water at room temperature. Therefore, gas sensors using these salts are too fragile to be applied in practical use.

Nevertheless, there is known a solid state gas sensor having a zirconia ceramic base on which auxiliary electrodes of a hard-to-sinter oxyacid salt such as a sulphate or a carbonate are provided.

Zirconia ceramic has a conductivity for oxygen ions and thus functions as a solid electrolyte when heated at an elevated temperature ranging from about 550° C. to about 1500° C., so that the difference between oxygen gas concentrations prevailing on the both sides of a zirconia ceramic base or substrate induces oxygen ion conduction through the base thickness to generate an electromotive force between opposite sides of the base. A gas sensor operates by measuring the thus-generated electromotive force.

FIG. 2 shows a sensor structure in which a sodium sulphate layer 206 is joined to the upper surface of a zirconia ceramic base 205 and a reference electrode 207 and a detecting electrode 208, both of platinum, are provided on the lower surface of the base 205 and the upper surface of the sodium sulphate layer 206.

This structure is different from the aforementioned gas sensor in that an auxiliary electrode 206 of sodium sulphate is provided on the zirconia ceramic base 205 to detect sulphur dioxide and other sulphur oxides.

To produce the above-recited gas sensors, it is important to form a crystal of a sulphate or a carbonate on a base. However, sulphates, carbonates, nitrates, etc. are not only hard to sinter but also easily decomposed and can hardly be applied in actual devices.

The above-mentioned second problem must be solved in order to form a crystal of a hard-to-sinter oxyacid salt such as a sulphate on, and joined to, a ceramic base such as zirconia ceramic.

There is also a third problem that, when a layer of a sulphate or the like is joined to a base of zirconia ceramic or other ceramic, interaction acting across the joint interface is week because the ceramic base has a smooth surface, so that the joined layer easily exfoliates from the base.

To solve this problem, the base surface is roughened or scratched to provide an increased strength of the joint between a sulphate layer and the base. However, this does not provide a sufficient solution because thermal shocks such as repeated heating and cooling readily cause exfoliation.

SUMMARY OF THE INVENTION

To solve the first problem, the first object of the present invention is to provide a solid electrolyte gas sensor simple in structure, compact in size, easy to operate, and easy to produce.

To solve the second problem, the second object of the present invention is to provide a process of producing a joined body of a ceramic member and a hard-to-sinter oxyacid salt crystal, in which a crystal of a hard-to-sinter oxyacid salt such as a sulphate, a carbonate, or a nitrate is well joined to a base of a ceramic such as zirconia ceramic without causing the crystal to crack.

To solve the third problem, the third object of the present invention is to provide a process of producing a crystal of a hard-to-sinter oxyacid such as a sulphate, a carbonate, a nitrate, etc. on and firmly joined to a ceramic base.

To achieve the first object according to the first aspect of the present invention, there is provided a solid electrolyte gas sensor comprising a base plate or substrate of a solid electrolyte on which are disposed a detecting electrode for detecting a selected gas, a reference electrode, and a conductor portion for an external connection such as an outer lead.

Preferably, a solid electrolyte gas sensor according to the present invention further comprises a heater unit disposed on the base plate for heating the base plate to the temperature at which the gas sensor operates.

In a solid electrolyte gas sensor according to the present invention, it is possible that plural detecting units are disposed on the base plate for detecting different gases, the detecting units each having a sensor for detecting a selected gas. In this case, it is preferred that the plural detecting units are disposed on one side of the base plate and a reference electrode commonly used for the plural detecting units is disposed on the other side of the base plate.

Preferably, the base plate is made of zirconia ceramic, the detecting electrode is disposed on one side of the base plate and the reference electrode is disposed on the other side of the base plate.

According to the first aspect of the present invention, the necessary conductor parts such as a detecting electrode and a reference electrode are formed on a base made of a solid electrolyte material in a monolithic form, so that a gas sensor using a solid electrolyte is easily produced by using a conventional method of firing ceramics and a conventional method of forming conductor parts on a ceramic base.

It is also advantageous to mount plural gas sensors on a single base for detecting different gas components, i.e., plural kinds of gases can be detected by a single device.

To achieve the second object according to the second aspect of the present invention, there is provided a process of producing a joined body of a ceramic member and a hard-to-sinter oxyacid salt crystal, the process comprising the steps of:

impregnating a porous ceramic plate having micropores extending through the entire thickness thereof, with a melt of a hard-to-sinter oxyacid salt such as a sulphate or a carbonate;

then cooling the impregnated ceramic plate to form a composite plate composed of the ceramic plate with the micropores filled with a crystal of the hard-to-sinter oxyacid salt; and joining the composite plate to a ceramic base.

In this process, a sulphate or the like is impregnated into a porous ceramic plate and is crystallized to form a composite plate in which a sulphate or the like is reinforced by the ceramic plate. The composite plate is then joined to a base so that the sulphate or the like is joined to the base.

The base or ceramic plate supporting the sulphate or the like must contain micro pores extending through the plate thickness in order to ensure direct joining of the sulphate or the like to the base or ceramic plate. The micro pores must be present in a large number sufficient to contain a substantial amount of the sulphate or the like. To this end, the ceramic plate is desirably produced by firing, using additives to ensure the formation of the necessary pores.

A sulphate or the like is conveniently impregnated into a porous ceramic plate by heating and melting the sulphate or the like to cause the melted sulphate to enter the ceramic plate. For example, the impregnation is effected by melting a powder of a sulphate or the like in a crucible and dipping a ceramic in the melted sulphate or the like.

The impregnated sulphate or the like is then cooled to crystallize, thereby providing a crystal of the sulphate or the like filled in the micro pores of the ceramic plate.

The thus-obtained ceramic plate or composite plate containing crystallized sulphate or the like is joined to a ceramic base to realize bonding of a crystal of a sulphate or the like to the ceramic base.

According to the second aspect of the present invention, a ceramic plate supports and reinforces a hard-to-sinter oxyacid such as a sulphate, so that cracking does not occur in the crystal of the sulphate or the like and the crystal is well joined to the ceramic base. Because the sulphate or the like is supported by the ceramic plate, decomposition of the sulphate or the like is effectively suppressed.

To achieve the third object according to the third aspect of the present invention, there is provided a process of producing a hard-to-sinter oxyacid salt crystal on, and joined to, a ceramic base, the process comprising the steps of:

forming a metal film on a ceramic base;

anodizing the metal film to form a porous oxide film having numerous micropores extending through the entire thickness thereof;

melting a hard-to-sinter oxyacid salt such as a sulphate or a carbonate on the porous oxide film, thereby causing the porous oxide film to be impregnated with a melt of the salt; and then cooling the ceramic base together with the oxide film to form a crystal of the hard-to-sinter oxyacid salt joined to the ceramic base.

The metal film may consist of aluminum or zirconium.

A metal film is formed on a base, on which a sulphate or the like is to be joined, the metal film is then oxidized by anodization to form an oxide film. A sulphate, carbonate, or the like is impregnated into the oxide film to crystallize, thereby producing a hard-to-sinter oxyacid crystal such as a sulphate or a carbonate on, and joined to, the base.

An oxide film is formed by anodization as mentioned above, in order to ensure the provision of pores in the oxide film, thereby providing an improved adhesion of the sulphate, carbonate, nitrate, or the like to the base. When this oxide film is applied to a gas sensor or other devices, the necessary ion conduction between the oxide film and the base is provided by the pores extending through the film thickness, which are easily formed by anodization.

A sulphate or a carbonate is impregnated into an oxide film by heating a powder thereof placed on the oxide film to form a melt, which is then allowed to flow into the pores of the oxide film. The melt impregnated in the oxide film is then cooled to form a crystal of the sulphate or carbonate on the base.

The sulphate or carbonate is joined to the base via the oxide film and therefore is firmly joined to the base with an improved joint strength by an anchoring effect of the oxide film so as not to exfoliate.

Metals easy to anodize to form a porous oxide film are suitably used to form a metal film on the base. Aluminum, zirconium, etc. are suitably used for this purpose. Aluminum is particularly advantageous in that a metal film is easily formed on a base by vapor deposition or sputtering and that a porous oxide film is easily formed by anodization. The method of forming a metal film on a base is, of course, not limited to these methods but may be any film forming method.

When an oxide film is formed on a base made of a solid electrolyte, as encountered in a gas sensor, care must be taken to avoid occurrence of chemical reactions between the oxide film and the base.

The present inventive process can be applied to producing various devices including the aforementioned solid state gas sensor, a solid state battery, etc.

DESCRIPTION OF THE PREFERRED EMBODIMENTS

Example 1

An embodiment according to the first aspect of the present invention will be described in detail with reference to the attached drawings.

Figure 1:
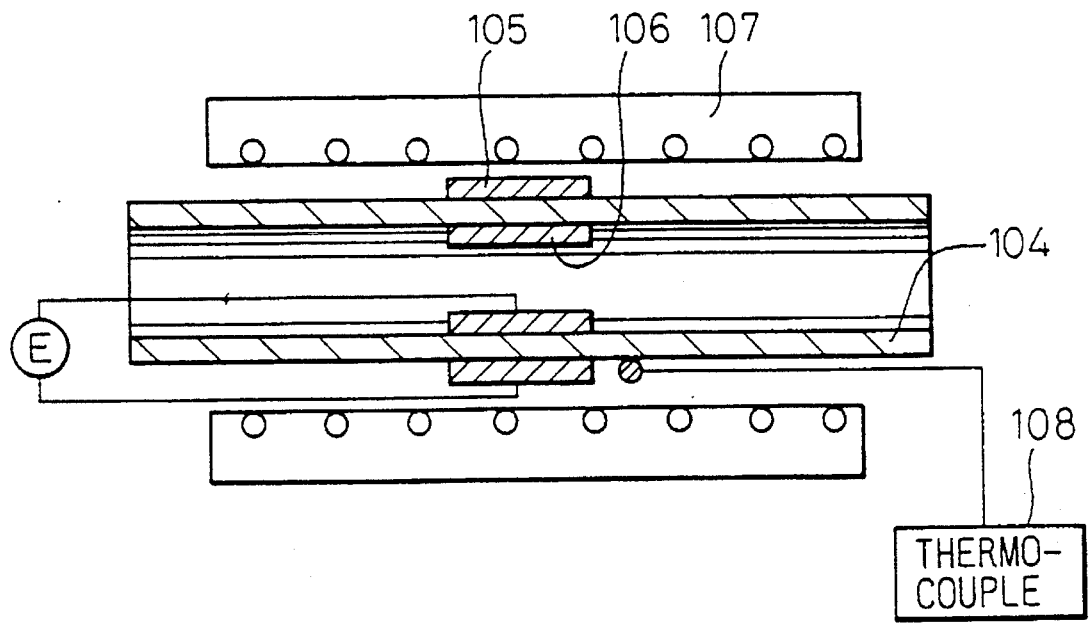
FIG. 1 shows a typical conventional solid electrolyte gas sensor, in a cross-sectional view.
Figure 2:
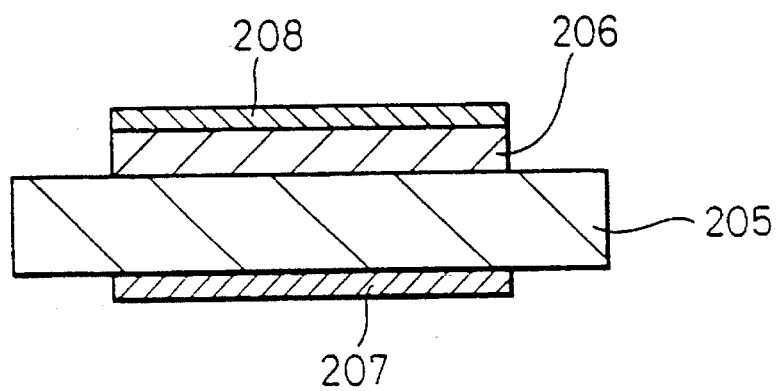
FIG. 2 shows another typical conventional solid electrolyte gas sensor, in a cross-sectional view.
Figure 3:
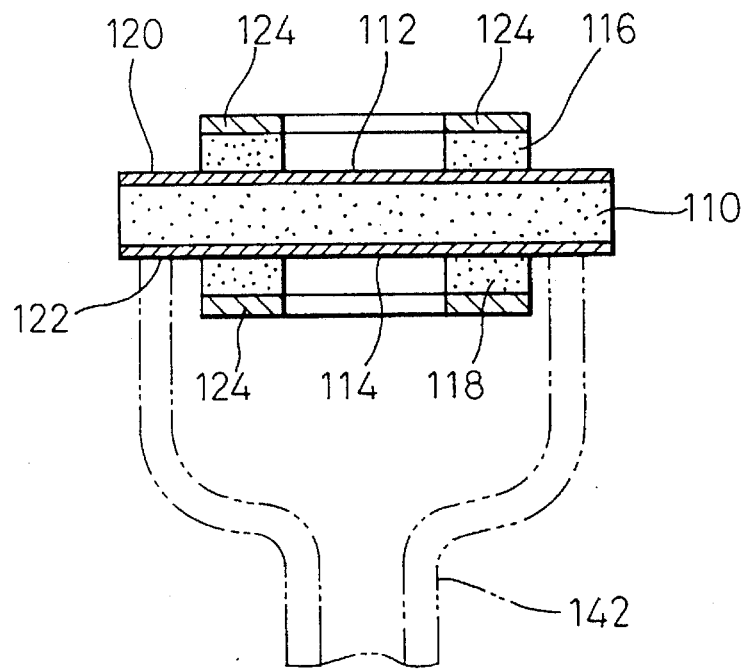
FIG.3 shows a solid electrolyte gas sensor according to the first aspect of the present invention.
Figure 4:
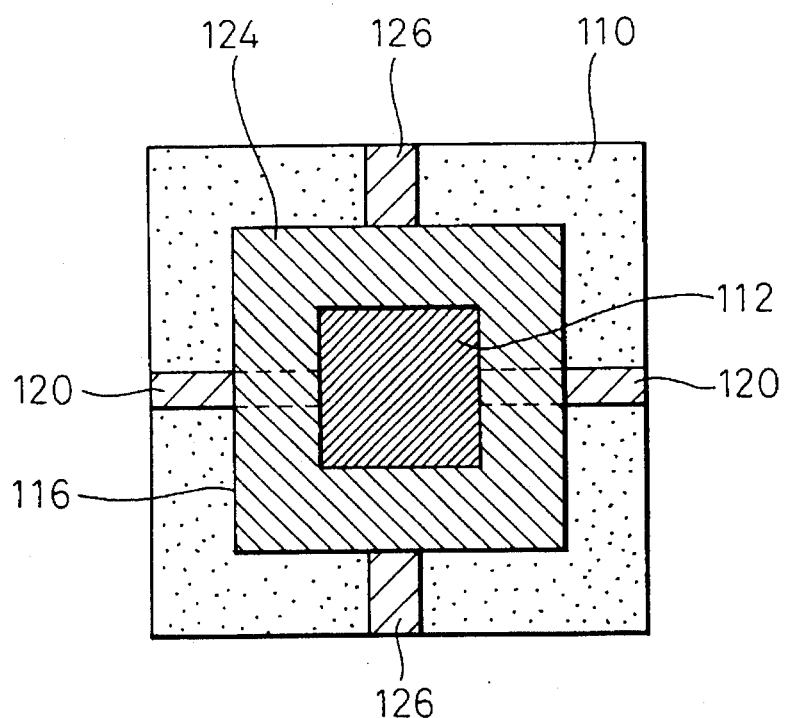
FIG. 4 shows the solid electrolyte gas sensor of FIG. 3, in a plan view.

FIGS. 3 and 4 show a oxygen gas sensor as an embodiment of the solid electrolyte gas sensor according to the present invention, in cross-sectional and plan views, respectively.

The shown sensor uses a solid electrolyte material of zirconia ceramic produced by firing a yttria-stabilized zirconia. The reference numeral 110 denotes a base of zirconia ceramic, 112 a detecting electrode provided on the upper surface of the base 110, and 114 a reference electrode provided on the lower surface of the base 110.

On the upper and lower surfaces of the base 110, rectangular frames 116 and 118, both of the same material as the base 110, are formed by firing. Detecting electrode 112 and reference electrode 114 are provided on the base 110 in the regions inside the frames 116 and 118. Outer leads 120 and 122 electrically connected to the detecting electrode 112 and the reference electrode 114 are provided on the upper and lower surfaces of the base 110. The outer leads 120 and 122 extend to the periphery of the base 110 and are used for external connection.

The reference numeral 124 denotes heaters provided on the frames 116 and 118. The heaters 124 are disposed over the entire top surfaces of the frames 116 and 118 as shown in FIG. 4 and heater leads 126 electrically connected to the heaters 124 are disposed on the base 110. The heater leads 126 run from the peripheries of the heaters 124 through the outer side walls of the frames 116 and 118 to the periphery of the base 110.

The heaters 124, the heater leads 126, the detecting electrode 112, the reference electrode 114, and the outer leads 120 and 122 are formed as conductors on the base and are made of platinum. To detect oxygen gas, the base 110 together with the conductors are heated to an elevated temperature, so that the conductors must be made of a heat resisting reliable metal. Metals other than platinum may used.

The above-mentioned solid electrolyte gas sensor is advantageously produced by using a technology for producing a ceramic package commonly used for semiconductor devices. Specifically, conductor patterns including the detecting electrode 112, the reference electrode 114, the outer leads 120 and 122, the heaters 124, and the heater leads 126 are formed by metallizing plural green sheets of zirconia ceramic with platinum, for forming the base 110 and the frames 116 and 118. The green sheets are then laminated and fired to provide a solid electrolyte gas sensor.

This solid electrolyte gas sensor detects the difference between the oxygen concentrations on the detecting electrode 112 and the reference electrode 114 and, for this purpose, these electrodes must be exposed to separate gas spaces isolated from each other.

The oxygen concentration measurement is performed by supplying electric current to the heaters 124 to heat the base 110 and detecting an electromotive force generated between the detecting electrode 112 and the reference electrode 114. Because the heaters 124 are adhered to the frames 116 and 118, heat generated in the heaters 124 is readily conducted to the base 110, so that the base 110 (zirconia ceramic) is readily heated to the elevated temperature of from 500° to 700° C. necessary to effect measurement, by supplying an electric current to the heater leads 126.

The solid electrolyte gas sensor of this embodiment advantageously has the detecting electrode 112 and the reference electrode 114 disposed on the zirconia ceramic base 110 and has the heater 124 disposed close to the oxygen detecting region of the zirconia ceramic base 110, so that the oxygen detecting region is readily heated to effect measurement and so that the simple and compact structure having conductors formed in the zirconia ceramic base 110 provides a gas sensor easy to produce and handle.

The solid electrolyte gas sensor of this embodiment uses zirconia ceramic as a solid electrolyte to detect the oxygen gas concentration and defines the oxygen gas detecting region by disposing the detecting electrode 112 and the reference electrode 114 with the base 110 interposed therebetween. Device shapes other than the rectangular one can be also easily provided because conductors having different shapes can be easily formed on the base 110 and because the shape of the frame or other portions of the base 110 can be differently designed. A composite gas sensor for detecting different gases can be produced by providing conductors and frames with selected patterns or shapes on the base and by providing detecting regions of the base for respective gases.

Figure 5:
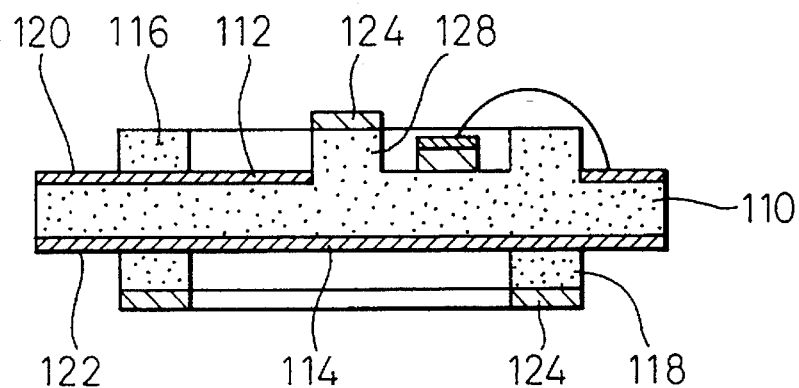
FIG. 5 shows another solid electrolyte gas sensor according to the first aspect of the present invention, in a cross-sectional view.
Figure 6:
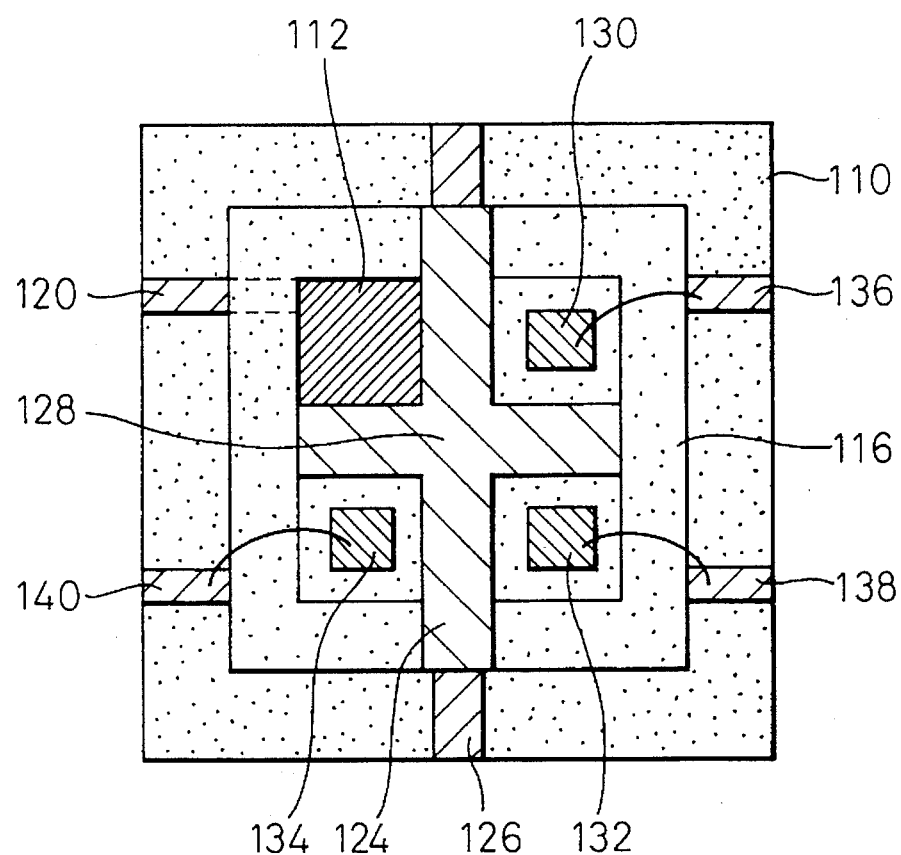
FIG. 6 shows the solid gas sensor of FIG. 5, in a plan view.

FIGS. 5 and 6 show an example of the solid electrolyte gas sensor designed for simultaneous detection of oxygen and other gases. This example also uses zirconia ceramic as a solid electrolyte, which is fired to form a base 110.

As can be seen from FIG. 6, the device has a frame 116 disposed on the base 110 in the same manner as that in the aforementioned example, and has a cross-shaped partition 128 inside the frame 116 to divide the inner area within the frame 116 into four detecting regions.

The four detecting regions can be provided with respective sensors to detect different gases, so that four different gases can be simultaneously detected.

In FIG. 6, the numeral 112 denotes a detecting electrode to detect oxygen gas, similarly in the aforementioned example. A similar frame 118 is disposed on the lower surface of the base 110 as was formerly shown in FIG. 3 and a reference electrode 114 is disposed entirely over the inner area within the frame 118. In the base region occupied by the detecting electrode 112, an oxygen gas sensor is composed of the detecting electrode 112, the reference electrode 114, and the zirconia ceramic of the base 110 interposed therebetween.

The other detecting regions 130, 132, and 134 are bounded by the partition 128 and the frame 116 to provide sensors on the base 110 for detecting gases other than oxygen gas, for example, SOx, COx, and NOx gases.

The sensors to detect these gases are formed by providing, on the zirconia ceramic base 110, auxiliary electrodes made of solid electrolytes having an ion conductivity for respective gases and by providing metal electrodes on the top surface of the respective solid electrolytes.

Outer leads 136, 138, and 140 are provided on the upper surface of the base 110 to conduct the respective signals from the sensors 130, 132, and 134 and are connected to these sensors by wire bonding or other connecting methods.

The reference electrode 114 provided on the lower surface of the base 110 serves as a common reference electrode to the respective sensors 130, 132, and 134.

The heaters 124 are disposed on the frames 118 on the lower side of the base 110 and on the top of the partition 128 on the upper side of the base 110. Measurement is conducted by heating the respective detecting regions by the heaters 124 to ensure a good ion conductivity.

The gas sensor of this embodiment has sensors for detecting different gases provided on the base 110 so that gases other than oxygen gas can also be detected.

As described hereinbefore, the conductors formed on the base 110 may have various shapes, so that the arrangement of the detecting regions in which the sensors 130,132, and 134 are disposed can be variously modified. It is also possible to detect more kinds of gases by increasing the number of the detecting regions defined in the base 110.

The solid electrolyte gas sensor according to the present invention is thus advantageous in that a wide selection of patterns of the device design, in accordance with various applications, is available.

The above-recited examples of the solid electrolyte gas sensor are not limited in application but can be provided as a device incorporating therein a gas sensor suitable for specific use. The device shown in FIG. 3 has a gas sensor sealingly fixed on one end of a cap-formed case 142.

Although the above-recited examples use zirconia ceramic as a solid electrolyte, the solid electrolyte gas sensor according to the present invention is not limited to those in which zirconia ceramic is used as a base. Other solid electrolytes having a good conductivity for ions of a specific gas component can be used to compose the same structure as described above to provide sensors for gases other than oxygen.

As mentioned above, the solid electrolyte gas sensor has a monolithic structure having a solid electrolyte base on which the necessary conductors for the detecting electrode and the reference electrode and the heaters are disposed, so that a compact and simple device is provided. The conductors are easily patterned in desired shapes by using known processes such as a process of firing ceramics in accordance with various applications. A plurality of sensors for detecting different gas components can be easily mounted on a single base to enable plural kinds of gases to be detected by a single device. Particularly, a sensor using zirconia ceramic as the solid electrolyte of a base is suitably used as an oxygen gas sensor.

Example 2

A preferred embodiment according to the second aspect of the present invention will now be described in detail by referring to the attached drawings.

In this example, sodium sulphate, as a hard-to-sinter oxyacid salt, was impregnated into a porous alumina ceramic plate, and crystallized in the pores of the alumina ceramic plate, which was then joined to a ceramic base. The porous alumina ceramic is a reinforcement member for supporting the crystal of sodium sulphate. Namely, the crystals formed in the numerous micropores of the porous alumina ceramic plate are advantageously joined to the ceramic base without causing cracking of the crystals.

In this example, the porous alumina ceramic plate was obtained by preparing an alumina slurry containing 25 vol % of resins such as polymethylmethacrylate as a component which will be dissipated by firing, forming a green sheet from the slurry by a doctor blade method, and firing the green sheet.

The sheet was fired by heating at 1° C./min from room temperature to 600° C., holding at 600° C. for 5 hours, and then heating at 1° C./min to 1300° C. to effect sintering.

The thus-obtained alumina ceramic plate contained about 45 vol % of pores.

The alumina ceramic plate was placed in a crucible containing therein a sodium sulphate powder and the crucible was then heated until the sodium sulphate powder was melted and impregnated into the alumina ceramic plate.

The heating process included heating at 3° C./min from room temperature to 920° C. and holding at 920° C. for 1 hour, followed by cooling at 1° C./min to 550° C., holding at 550° C. for 5 hours, and cooling at 3° C./min to room temperature. At 550° C. a phase transformation occurs and the holding at this temperature suppresses the occurrence of cracking induced by a volume change during the phase transformation.

This provided a composite plate composed of an alumina ceramic plate having micropores filled with crystals of the impregnated sodium sulphate.

An observation of the alumina ceramic plate impregnated with sodium sulphate showed that the micropores are filled with the sodium sulphate in the form of a sound or complete crystal containing no cracks. This is thought to be because the alumina ceramic plate acts as a reinforcing member for the sodium sulphate crystal to prevent the occurrence of cracking in the sodium sulphate crystal. As the sodium sulphate is supported by an alumina ceramic plate, decomposition of the sodium sulphate by absorbing the environmental water is advantageously prevented.

When a hard-to-sinter oxyacid salt such as a sulphate or a carbonate is impregnated into and supported by a porous ceramic plate, the base ceramic plate preferably has about 45 to 50% of pores to ensure a good crystal structure.

Figure 7:
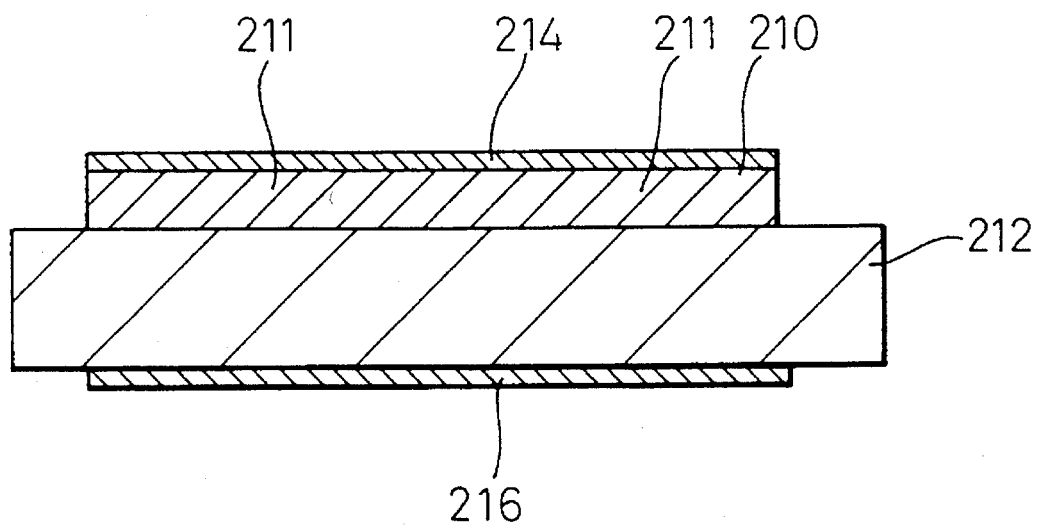
FIG. 7 shows a joined body of a ceramic member and a hard-to-sinter oxyacid salt crystal according to the second aspect of the present invention, in a cross-sectional view.

FIG. 7 shows a solid-state gas sensor having an alumina ceramic plate 210 containing crystals of sodium sulphate impregnated therein in the above-mentioned manner. The alumina ceramic plate 210 is porous and, specifically, has micropores filled with crystals of the sodium sulphate 211.

The alumina plate 210 is joined to a zirconia ceramic base 212. A detecting electrode 214 and a reference electrode 216 are formed on the upper surface of the alumina ceramic plate 210 and the lower surface of the base 212 by depositing platinum thereon.

The shown gas sensor measures the gas concentration by measuring the electromotive force between the detecting electrode 214 and the reference electrode 216 and, particularly, detects sulphur oxide gases based on the fact that the zirconia ceramic of the base 212 act as a solid electrolyte having a conductivity for oxygen ions while sulphuric acid ions are conducted through the sodium sulphate.

The sodium sulphate 211 is impregnated and crystallized in the alumina ceramic plate 210 and is thus joined to the base 212 with its sound crystal structure preserved so as to provide the ion conduction necessary to ensure effective operation as a gas sensor. The alumina ceramic plate 210 supports the sodium sulphate 211 to provide high impact resistance and also suppresses decomposition of the sodium sulphate to provide improved durability.

It is also feasible to make a multiple-layered structure by laminating plural pieces of the alumina ceramic plate containing the impregnated crystals of sodium sulphate as obtained in this example.

The alumina ceramic plate containing the impregnated sulphate or the like is advantageously utilized to produce gas sensors or other devices having laminated layers of sodium sulphate or the like containing various additives to improve the ion conductivity.

When the base 212 has a smooth surface, which reduces the joint strength between the sodium sulphate-impregnated alumina ceramic plate 210 and the base 212, the latter is desirably subjected to a treatment to improve the joint strength.

A preferred treatment includes depositing an aluminum or other metal film on the base surface to which sodium sulphate is to be joined and anodizing the metal film to form a porous oxide film. The thus-formed porous oxide film provides an anchoring effect to ensure a strong joint between the base 212 and the alumina ceramic plate 210 impregnated with a sulphate or the like.

The alumina ceramic plate 210 is joined to the base 212 by heating and melting a sodium sulphate powder on the oxide film. The thus-obtained joint has a high long term reliability. When the long term reliability is not important, the base surface may be roughened as in the conventional treatment.

The oxide film does not adversely affect the ion conduction, but is easily made porous by anodizing the metal film to provide a strong joint between a sulphate or the like and the base 212.

Although sodium sulphate is used as the hard-to-sinter oxyacid salt in this example, this embodiment can be similarly applied to other sulphates, and further, to carbonates, nitrates, etc. Although alumina ceramic was used as a reinforcing member for the sodium sulphate, ceramics other than alumina ceramic can be also used.

Although this example describes a gas sensor to which the present invention is applied, the present invention can be also applied to devices other than gas sensors.

As mentioned above, according to the process of producing a joined body of a ceramic member and a hard-to-sinter oxyacid salt crystal, crystals of hard-to-sinter oxyacid salt such as a sulphate, a carbonate, or the like are supported or reinforced by a ceramic plate and thereby joined to a base without causing cracking of the crystals. Water absorption by the sulphate or the like is also suppressed to prevent decomposition thereof, so that hard-to-sinter oxyacid salts can be applied to practical use.

Example 3

A preferred embodiment according to the third aspect of the present invention will now be described in detail with reference to the attached drawings.

In this example, a fired body of a yttria-stabilized zirconia ceramic is used as a base, on which crystals of sodium sulphate as a hard-to-sinter oxyacid salt are formed.

Figure 8:
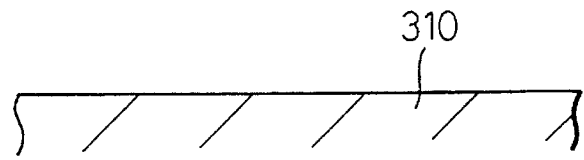
FIG. 8 shows a ceramic base on which a hard-to-sinter oxyacid salt crystal is to be formed, being joined to the ceramic base, in a cross-sectional view.

FIGS. 8 to 11 are sectional views showing a process sequence of forming crystals of sodium sulphate on a base 310. FIG. 8 shows a base 310 of fired zirconia ceramic.

Figure 9:
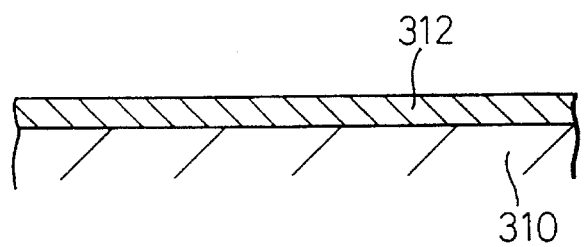
FIG. 9 shows the base of FIG. 8 on which a metal film is formed, in a cross-sectional view.

First, aluminum was vapor-deposited on the base 310 to form a metal film 312 (FIG. 9).

Figure 10:
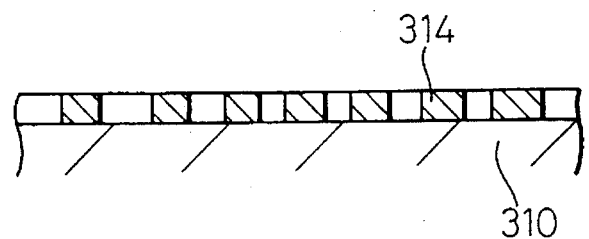
FIG. 10 shows a porous metal oxide film formed by anodizing the metal film of FIG. 9, in a cross-sectional view.

The metal film 312 was then oxidized by anodization. FIG. 10 shows an oxide film 314 obtained by oxidizing the metal film 312. In this example, anodizing the metal film 312 of aluminum provided an alumina coating.

The metal film 312 was anodized until the base surface was exposed through the porous oxide film 314. A suitably selected anodizing solution provides a desired porous condition because of a simultaneous oxidation of aluminum and partial dissolution of the alumina.

In this example, the metal film 312 was anodized in a 4.25% phosphoric acid solution composed of 20 ml phosphoric acid and 380 ml pure water, by placing the sample on the anode and using a carbon cathode. The maximum applied voltage was 150 V and a current of 5 mA was applied for 1 hour.

The sample coated with an alumina film was then dried at 120° C. for 1 hour. An observation of the sample showed that the porous oxide film 314 partially exposed the base 310 therethrough.

Figure 11:
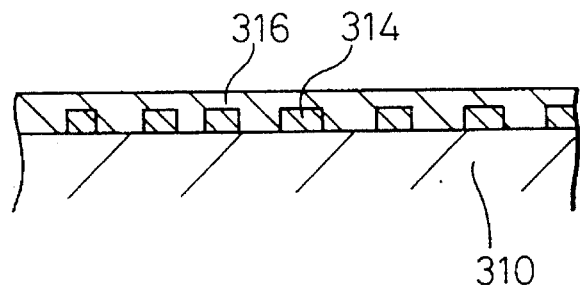
FIG. 11 shows crystals of hard-to-sinter oxyacid formed in numerous micro pores of the porous metal oxide film of FIG. 10 by impregnating a melted hard-to-sinter oxyacid salt into the metal oxide film followed by cooling, in a cross-sectional view.

The base 310 with a sodium sulphate powder placed on the oxide film 314 was heated to above the melting point of sodium sulphate to melt the sodium sulphate. The melted sodium sulphate entered the micropores in the porous oxide film 314 and was crystallized by the subsequent cooling. FIG. 11 shows a layer of sodium sulphate 316 formed on the base 310.

It can be seen from the figure that the sodium sulphate 316 entered the pores and was crystallized there. The sodium sulphate 316 is joined to the base 310 with a high joint strength by the anchoring effect of the oxide film 314.

An exfoliation test using thermal impact showed that the sodium sulphate 316 did not exfoliate, i.e., had a high joint strength.

It was also proved that the sodium sulphate 316 had a sound crystal structure containing no cracks.

This embodiment is also advantageous in that the oxide film 314 is composed of alumina and does not chemically react with the zirconia ceramic of the base 310.

Although zirconia ceramic was used as a base, other ceramics such as alumina may be also used as a base.

As described hereinabove, the present invention securely joins a crystal of a hard-to-sinter oxyacid salt such as a sulphate or a carbonate to a ceramic base and thereby provides an advantage that gas sensors and other devices having a hard-to-sinter oxyacid salt as a component have an improved durability sufficient for practical application.

We claim:

1. A solid electrolyte gas sensor comprising:

a base plate of an oxygen ion conductive solid electrolyte on which are disposed a plurality of detecting units for detecting oxygen and other selected gases, each unit comprising a detecting electrode and each unit for detecting one of said other gases further comprising a solid electrolyte conductive to ions of said one of said other gases, a reference electrode commonly used in conjunction with all the detecting units and a conductor portion for external connection, wherein the detecting units are disposed on one side of said base plate, and wherein the reference electrode is disposed on the other side of the base plate.

2. A solid electrolyte gas sensor according to claim 1, further comprising a heater unit disposed on said base plate for heating said base plate to a temperature at which said gas sensor is operated.

3. A solid electrolyte gas sensor according to claim 2, wherein said base plate is made of zirconia ceramic, said detecting electrodes are disposed on one side of said base plate and said reference electrode is disposed on the other side of said base plate.

4. A solid electrolyte gas sensor according to claim 1, wherein said base plate is made of zirconia ceramic, said detecting electrodes are disposed on one side of said base plate and said reference electrode is disposed on the other side of said base plate.

5. A solid electrode sensor according to claim 1, wherein the conductor portion for external connection is an external lead.

* * * * *